United States Patent
Harris et al.

(10) Patent No.: US 11,583,170 B2
(45) Date of Patent: Feb. 21, 2023

(54) DEVICES FOR TREATMENT OF BODY LUMENS

(71) Applicant: Boston Scientific Scimed, Inc., Maple Grove, MN (US)

(72) Inventors: Colby Harris, Weston, MA (US); Paul Smith, Smithfield, RI (US); James J. Scutti, Arlington, MA (US); Louis J. Barbato, Franklin, MA (US); Ryan Evers, Billerica, MA (US); Dane Seddon, Boston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 398 days.

(21) Appl. No.: 16/525,652

(22) Filed: Jul. 30, 2019

(65) Prior Publication Data
US 2020/0037863 A1 Feb. 6, 2020

Related U.S. Application Data

(60) Provisional application No. 62/713,669, filed on Aug. 2, 2018.

(51) Int. Cl.
*A61B 1/00* (2006.01)
*A61B 1/05* (2006.01)

(52) U.S. Cl.
CPC ...... *A61B 1/00183* (2013.01); *A61B 1/00082* (2013.01); *A61B 1/00087* (2013.01); *A61B 1/05* (2013.01)

(58) Field of Classification Search
CPC ............ A61B 1/00183; A61B 1/00087; A61B 1/05; A61B 1/012; A61B 1/0058; A61B 1/0008
See application file for complete search history.

(56) References Cited

U.S. PATENT DOCUMENTS

| 6,071,233 | A | * | 6/2000 | Ishikawa | ............... | A61B 1/0014 |
| | | | | | | 600/104 |
| 7,922,650 | B2 | * | 4/2011 | McWeeney | ....... | A61M 25/0068 |
| | | | | | | 600/104 |
| 8,235,887 | B2 | | 8/2012 | Bayer et al. | | |
| 8,289,381 | B2 | | 10/2012 | Bayer et al. | | |

(Continued)

FOREIGN PATENT DOCUMENTS

WO 00/62699 A2 10/2000
WO 2006/116558 A2 11/2006

*Primary Examiner* — Aaron B Fairchild
*Assistant Examiner* — Shankar Raj Ghimire
(74) *Attorney, Agent, or Firm* — Bookoff McAndrews, PLLC

(57) ABSTRACT

A medical device may comprise a handle portion; an insertion portion having a proximal end portion at the handle portion, wherein the insertion portion includes a lumen therein and a distal end having a distal opening in communication with the lumen; and a member disposed within the lumen, the member having a distal end portion with an imaging device. The member may be configured to transition between a first configuration and a second configuration. In the first configuration, the imaging device may face distally, and, in the second configuration, the imaging device may face proximally. Extending the distal end portion of the member distally past the distal opening may cause the member to transition from the first configuration to the second configuration.

20 Claims, 10 Drawing Sheets

(56) References Cited

U.S. PATENT DOCUMENTS

| | | | |
|---|---|---|---|
| 9,498,112 B1* | 11/2016 | Stewart | A61B 1/0058 |
| 2001/0049509 A1* | 12/2001 | Sekine | A61B 1/018 |
| | | | 600/104 |
| 2004/0049095 A1* | 3/2004 | Goto | A61B 1/00098 |
| | | | 600/107 |
| 2005/0119525 A1* | 6/2005 | Takemoto | A61B 1/00137 |
| | | | 600/114 |
| 2005/0251176 A1* | 11/2005 | Swanstrom | A61B 17/1114 |
| | | | 606/153 |
| 2005/0272977 A1* | 12/2005 | Saadat | A61B 1/00183 |
| | | | 600/114 |
| 2006/0189845 A1* | 8/2006 | Maahs | A61B 1/018 |
| | | | 600/146 |
| 2007/0142711 A1* | 6/2007 | Bayer | A61B 1/0676 |
| | | | 600/175 |
| 2007/0177009 A1* | 8/2007 | Bayer | A61B 1/05 |
| | | | 348/65 |
| 2007/0225734 A1* | 9/2007 | Bell | A61B 17/12013 |
| | | | 606/139 |
| 2007/0287886 A1 | 12/2007 | Saadat | |
| 2008/0021274 A1* | 1/2008 | Bayer | A61B 1/00137 |
| | | | 600/117 |
| 2008/0130108 A1* | 6/2008 | Bayer | A61B 1/00096 |
| | | | 359/489.07 |
| 2008/0243176 A1* | 10/2008 | Weitzner | A61B 1/00154 |
| | | | 606/206 |
| 2008/0262301 A1* | 10/2008 | Gibbons | A61B 1/01 |
| | | | 600/114 |
| 2008/0287963 A1* | 11/2008 | Rogers | A61B 34/71 |
| | | | 606/130 |
| 2009/0213211 A1* | 8/2009 | Bayer | H04N 5/3651 |
| | | | 348/65 |
| 2009/0231419 A1* | 9/2009 | Bayer | A61B 1/0125 |
| | | | 348/76 |
| 2012/0041533 A1* | 2/2012 | Bertolino | A61B 1/00181 |
| | | | 623/1.11 |
| 2012/0053485 A1 | 3/2012 | Bloom | |
| 2013/0172677 A1 | 7/2013 | Kennedy, II et al. | |
| 2013/0331343 A1 | 12/2013 | Cao et al. | |
| 2016/0174814 A1* | 6/2016 | Igov | A61B 17/0218 |
| | | | 600/106 |
| 2016/0174820 A1* | 6/2016 | Dejima | A61M 39/06 |
| | | | 600/114 |
| 2016/0317233 A1 | 11/2016 | Hunter et al. | |
| 2016/0331343 A1 | 11/2016 | Hunter et al. | |
| 2017/0231474 A1* | 8/2017 | Saadat | A61B 1/00098 |
| | | | 600/107 |
| 2019/0059942 A1* | 2/2019 | Watson | A61B 17/3421 |
| 2019/0060014 A1* | 2/2019 | Hazelton | A61B 34/35 |
| 2020/0037863 A1* | 2/2020 | Harris | A61B 1/05 |

* cited by examiner

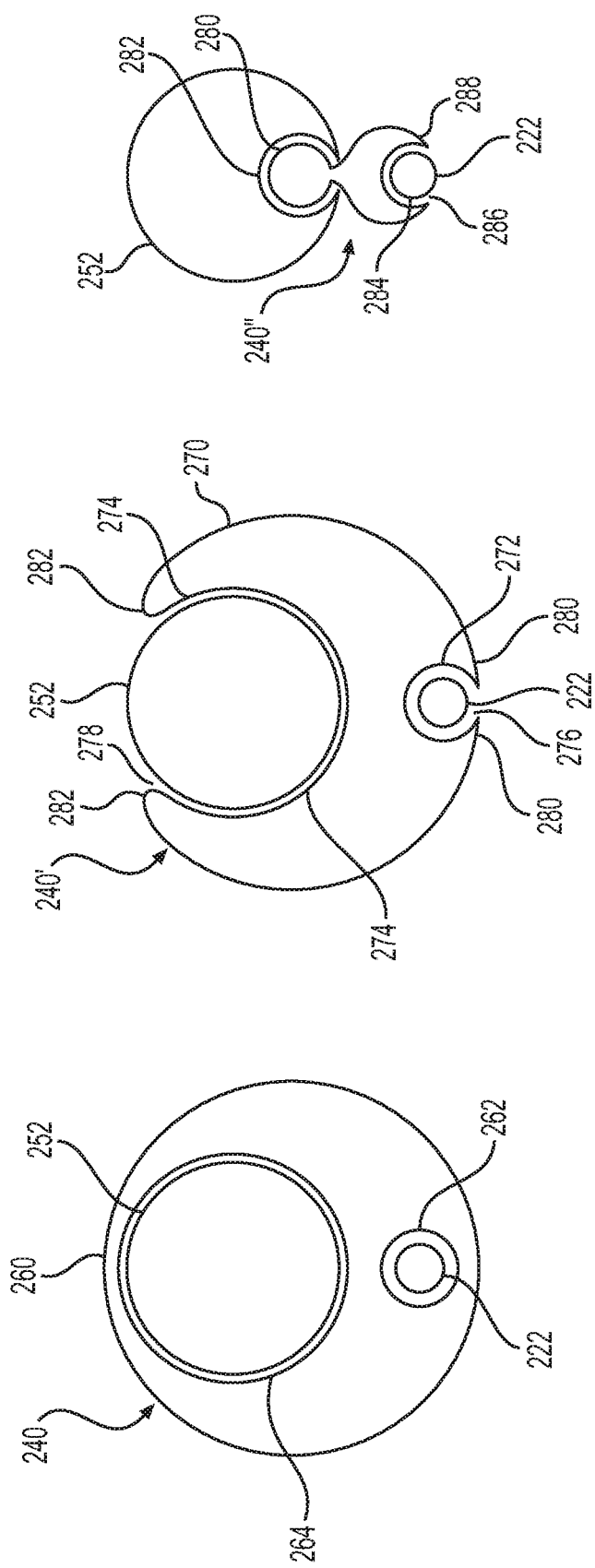

DEVICES FOR TREATMENT OF BODY LUMENS

CROSS-REFERENCE TO RELATED APPLICATIONS

This application claims the benefit of priority from U.S. Provisional Application No. 62/713,669, filed on Aug. 2, 2018, which is incorporated by reference herein in its entirety.

TECHNICAL FIELD

The present disclosure relates generally to devices and methods for diagnosing and/or treating tissue using, for example, endoscopes, bronchoscopes, and ureteroscopes. More specifically, aspects of the present disclosure pertain to devices and methods for positioning and/or visualizing medical devices within body lumens of a subject.

BACKGROUND

Endoscopic, bronchoscopic, or ureteroscopic techniques may be used for diagnosing, treating, and/or monitoring conditions by advancing tools and other devices through body lumens. However, it may be difficult to perform procedures in certain body lumens due to a narrow diameter of the lumen. For example, it may be difficult to obtain a biopsy or to treat a nodule or lesion in the periphery of the lungs, due to an inability to visualize the periphery lumen using traditional endoscopes. Typical therapeutic and diagnostic endoscopes may be limited in how many generations of the bronchi they are able to navigate due to their relatively large outer diameter of approximately 6 mm or greater. Many current procedures for obtaining a biopsy of a nodule or lesion in the fifth or higher generation of the bronchi tend to be done blind because of the lack of an optics system compatible with biopsy devices and small enough to provide visualization of peripheral airways. A lack of visualization may lead to (a) low yields and/or (b) increased procedure time resulting from a user's needing to spend additional time to ensure that a tool is positioned in the correct location.

SUMMARY

Examples of the present disclosure relate to, among other things, devices and methods for positioning and/or visualizing medical devices within body lumens of a subject. Each of the examples disclosed herein may include one or more of the features described in connection with any of the other disclosed examples.

A medical device may comprise a handle portion; an insertion portion having a proximal end portion at the handle portion, wherein the insertion portion includes a lumen therein and a distal end having a distal opening in communication with the lumen; and a member disposed within the lumen, the member having a distal end portion with an imaging device. The member may be configured to transition between a first configuration and a second configuration. In the first configuration, the imaging device may face distally, and, in the second configuration, the imaging device may face proximally. Extending the distal end portion of the member distally past the distal opening may cause the member to transition from the first configuration to the second configuration.

Any medical device described herein may include one or more of the features described below. The member may include a flat shaft having a cross sectional width greater than a thickness and having at least one substantially planar outer surface. The shaft may be ribbon shaped. The imaging device may be disposed on a side surface of the member. On the first configuration, the distal end portion of the member may form approximately a right angle relative to a more proximal portion of the member. In the second configuration, the distal end portion of the member may form a curl shape. The member may be configured to transition between the first configuration and the second configuration by moving the member longitudinally relative to the lumen. A proximal portion of the member may be coupled to a hub. The hub may be configured to effect longitudinal movement of the member relative to the lumen as the hub translates relative to the handle portion. The lumen may be in communication with a first proximal opening in the handle portion and with a second proximal opening in the handle portion. A tool may be insertable into at least one of the first and second opening. A first proximal lumen and a second proximal lumen may join to form the lumen. The member may rest against a side surface of the lumen so that a tool may be disposed in the lumen along with the member. In the first configuration, a side surface of the lumen may engage a surface of the member. The member may transition from the first configuration to the second configuration due to a shape memory of the member. The insertion portion may further comprise a second lumen.

A method of treatment may comprise: advancing an insertion portion of a medical device in a body lumen of a subject; visualizing the body lumen using an imaging device of a member, wherein the member is disposed in a lumen of the insertion portion, and wherein the imaging device faces distally out of a distal opening of the lumen; moving the member longitudinally relative to the lumen, causing the imaging device to be located distally of the distal opening of the lumen and to face proximally; after moving the member, visualizing the body lumen using the imaging device; inserting a tool into the lumen of the insertion portion; and performing a procedure using the tool.

Any method described herein may include one or more of the features or steps described below. Moving the member may include sliding a hub at a proximal portion of the member, relative to a handle portion of the medical device. The member may include a flat shaft having a cross sectional width greater than a thickness and having at least one substantially planar outer surface. The shaft may be ribbon shaped. After moving the member, a distal end portion of the member may form a curl shape. A second tool may be inserted into a second lumen of the member.

A medical device may comprise: a member having a shaft, an imaging device, and an anchor member; a tool having a shaft; and a tether, comprising: a first surface, wherein the first surface is configured so as to slidably engage with the shaft of the member; and a second surface, wherein the second surface is configured so as to engage with the shaft of the tool to secure the tether to the tool as the tether slides relative to the member.

Any medical device described herein may include one or more of the features described below. The member may be configured to transition between a first configuration and a second configuration. In the first configuration, the imaging device may face distally. On the second configuration, the imaging device may face proximally. The first surface may define a first lumen for engaging the shaft of the member, and the second surface may define a second lumen for engaging the shaft of the tool. A surface of the tether may include an opening in communication with at least one of the first and second lumens. The anchor member may include at least one of the following: an inflatable member, a clip, and a coil. A steering mechanism may have a shaft. The second surface may be configured so as to engage with the steering mechanism to secure the tether to the steering mechanism as the tether slides relative to the member.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." The term "endoscope" may be used herein but is not limiting. References to endoscopes may also include other medical devices, including, but not limited to, bronchoscopes and ureteroscopes.

BRIEF DESCRIPTION OF THE DRAWINGS

The accompanying drawings, which are incorporated in and constitute a part of this specification, illustrate examples of the present disclosure and together with the description, serve to explain the principles of the disclosure.

FIGS. 7A-7C show cross-sectional schematic views of exemplary tethering devices.

DETAILED DESCRIPTION

The present disclosure is drawn to devices, systems, and/or methods for diagnosing and/or treating tissue using, for example, endoscopes, bronchoscopes, and ureteroscopes. More specifically, aspects of the present disclosure pertain to devices and methods for positioning and/or visualizing tools and/or devices within body lumens of a subject. In particular, in at least some aspects, the devices and methods disclosed herein may provide for visualization of an area of interest in a narrow passageway such as a bronchus. The devices and methods disclosed herein may facilitate advancement of tools to a visualized area of interest. Although respiratory anatomy may be referenced herein, reference to respiratory anatomy should not be construed as limiting possible applications of the disclosed devices and methods. The disclosed devices and methods may be suitable for use in a variety of portions of a subject's body, including, for example, urological organs or the digestive system.

Figure 1:
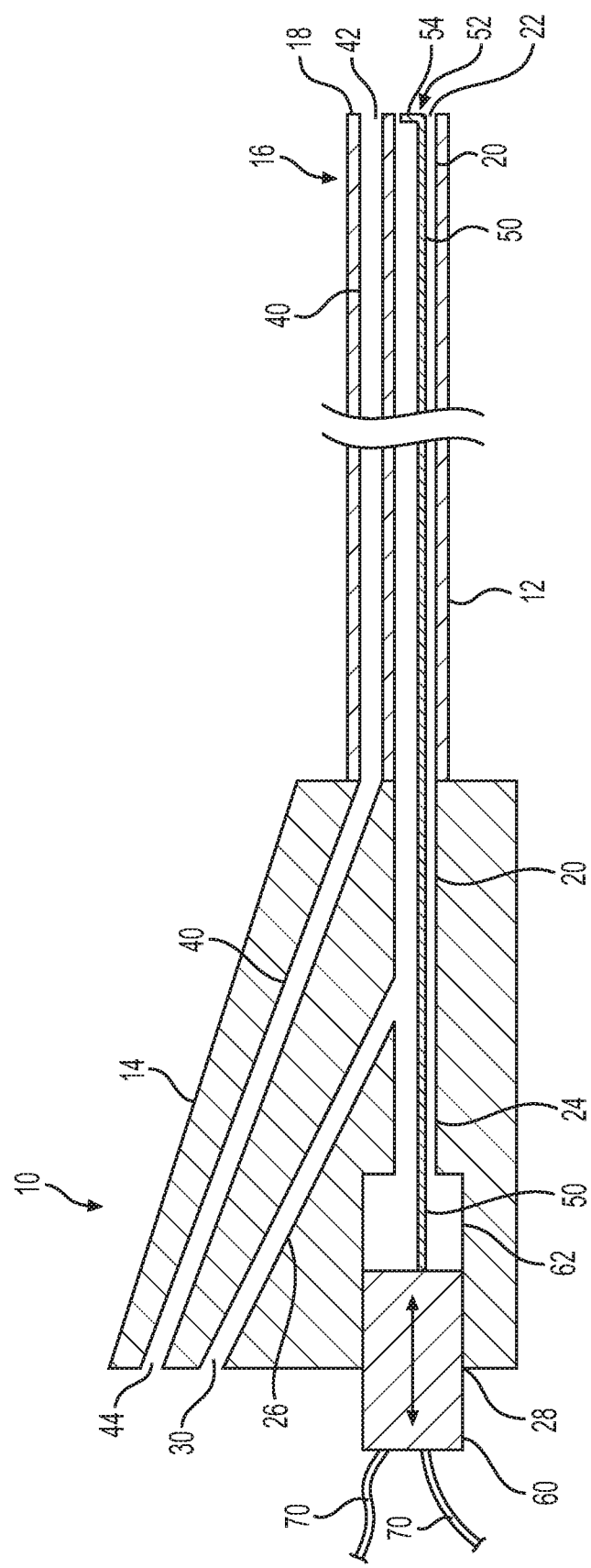
FIG. 1 shows a schematic cross-section of an exemplary device in a first configuration.
Figure 2:
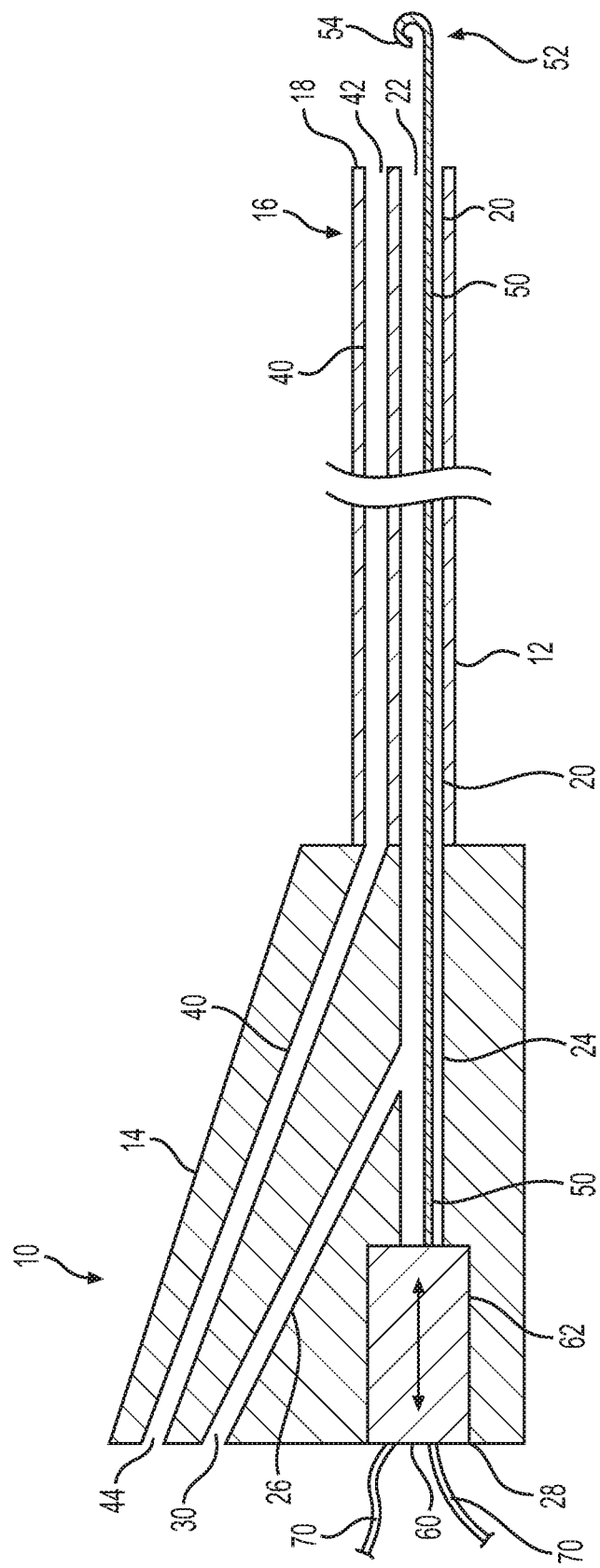
FIG. 2 shows a schematic cross-section of an exemplary device in a second configuration.

FIGS. 1-2 depict a medical device 10, which may have an insertion portion 12 and a handle portion 14. A proximal end portion of insertion portion 12 may be connected to a distal portion of handle portion 14. Insertion portion 12 may be disposed distally of handle portion 14 relative to an operator of device 10. Medical device 10 may be a device, such as an endoscope, ureteroscope, bronchoscope, or other type of scope, catheter, or sheath. Insertion portion 12 may be inserted into a subject. For example, insertion portion 12 may be inserted into a body lumen of a subject. Insertion portion 12 may be an elongate member such as a shaft and may have a longitudinal axis. Insertion portion 12 may be steerable by any suitable mechanism.

Insertion portion 12 may have a distal end portion 16, including a distal end face 18. A lumen 20 may be within insertion portion 12. For example, lumen 20 may extend from a proximal portion of insertion portion 12 to distal end portion 16 of insertion portion 12. A longitudinal axis of lumen 20 may be coaxial with or parallel to a longitudinal axis of insertion portion 12. Lumen 20 may lead to a distally-facing opening 22 in distal end face 18. Lumen 20 may also include a first proximal portion 24, which may extend into handle portion 14. Lumen 20 may also include a second proximal portion 26. For example, lumen 20 may diverge into two proximal portions 24 and 26 at a y-shaped or otherwise shaped junction. Proximal portion 24 may lead to an opening 28 in handle portion 14. Proximal portion 26 may lead to an opening 30 in handle portion 14. Thus, lumen 20 may be bifurcated, with two separate access points (opening 28 and opening 30) providing access to lumen 20.

Insertion portion 12 may also optionally include a second lumen 40. Second lumen 40 may lead to a distal opening 42 in distal end face 18. Second lumen 40 may also lead to an opening 44 in handle portion 14. In addition or in an alternative, second lumen 40 may lead to openings 28 and/or 30.

A member 50 may be inserted in lumen 20. Member 50 may have an elongated shape. Member 50 may extend from proximal portion 24 of lumen 20 toward opening 22. Member 50 may be flat or ribbon-shaped. In an alternative, member 50 may not be flat but may have a first flat surface and a second flat surface. Side surfaces connecting the flat surfaces may be short so that member 50 is substantially flat. In an alternative, member 50 may have a circular, polygonal, ovular, or other cross-section. Member 50 may be made at least partially from nitinol and may be made from a nitinol ribbon. Member 50 may exhibit shape memory.

Member 50 may include a distal portion 52. Distal portion 52 of member 52 may include a camera portion 54. Camera portion 54 may be disposed on a surface of distal portion 52 of member 50. Signal cables may be operative to provide power to camera portion 54, provide control signals to camera portion 54, and/or retrieve images from camera portion 54. Such signal cables may be adhered or otherwise attached to a surface of member 50 or embedded within member 50. For example, signal cables may extend from a proximal portion of member 50 toward distal portion 52 of member 50. Member 50 may also include other electronics, such as illumination components. For example, member 50 may include one or more light emitting diodes (LEDs) such as surface LEDs, printed LEDs, or other suitable devices.

A proximal portion of member 50 may be coupled to a hub 60. Hub 60 may be formed of any suitable material, such as the same material comprising member 50 or a material comprising handle portion 14. Hub 60 may be slidably disposed in a mating cavity 62 of handle portion 28. Hub 60 may have a clearance fit with mating cavity 62. One or more cables 70 may extend from a proximal portion of hub 60 and may provide power and/or control signals to camera portion 54 and/or transmit image data from camera portion 54. Cables 70 may extend through or along hub 60 and along member 50 from a proximal portion of member 50 toward a distal portion 52 of member 50. In addition or in an alternative, cables 70 may be electrically coupled to other cables which extend through or along hub 60 and/or along member 50.

Sliding hub 60 relative to handle portion 14 and insertion portion 12 may cause movement of member 50 relative to handle portion 14 and/or insertion portion 12. For example, sliding movement of hub 60 proximally or distally may cause member 50, including distal portion 52 of member 50, to move longitudinally (proximally or distally, respectively) relative to insertion portion 12. Hub 60 may be connected to an actuator for effecting such sliding motion, or a user may effect a sliding motion via hub 60 alone. Longitudinal movement of member 50 via, e.g., hub 60, may cause member 50 to transition from a first configuration (FIG. 1) to a second configuration (FIG. 2). In a first configuration (FIG. 1), a distal portion 52 of member 50, including camera portion 54, may be located at or near opening 22 of lumen 20. For example, distal portion 52 and/or camera portion 54 may be slightly longitudinally proximal to opening 22, aligned with opening 22, or slightly distal to opening 22. In the first configuration, distal portion 54 may curve upward so that distal portion 54 forms roughly a right angle with respect to more proximal portions of member 50, as shown in FIG. 1. In such a configuration, camera portion 54 may face distally away from distal face 18, out of opening 22.

In a second configuration (FIG. 2), distal portion 52 of member 50, including camera portion 54, may be located distally of opening 22 of lumen 20. In the second configuration, distal portion 52 of member 50 may be curved upward and backward (in the proximal direction). In either the first or the second configuration, member 50 may curve smoothly, so that no sharp angles are formed in member 50. In an alternative, member 50 may include angled and/or hinged portions in distal portion 52. In the second configuration, camera portion 54 may face proximally, toward handle 14. A proximal orientation of camera portion 54 may also include other directional components. For example, in addition to facing proximally, camera portion 54 may also face an upward or downward direction (a direction transverse to the longitudinal axis of member 50). For example, in FIG. 2., proximally-facing camera portion 54 also faces upward in a direction transverse to the axis. In the second configuration, member 50 may roll or curl back on itself by at least 180 degrees with camera portion 54 mounted on an outward-facing surface of member 50 near an end of the formed curl.

Member 50 may be biased to assume the shape of the second configuration or, in other words, member 50 may be biased so that camera portion 54 faces proximally. For example, member 50 may have shape memory. When member 50 is in the first configuration, the size and shape of lumen 20 may prevent member 50 from facing proximally. For example a portion of distal portion 52 may interact with an interior surface of lumen 20 and/or opening 22. For example, a distal edge of member 50 may interact with a top surface, a bottom surface, and/or a side surface of lumen 20 and/or opening 20. Movement of hub 60, which may be connected to a proximal portion of member 50, may cause member 50 to transition from the first configuration to the second configuration, and from the second configuration to the first configuration. When hub 60 is moved distally, member 50 may transition to the second configuration. For example, member 50 may transition due to removal of engagement of distal end portion 52 with one or more inner surfaces of lumen 20 and/or opening 22. Member 50 may transition due to shape memory or other biasing of member 50. When hub 60 is moved proximally, member 50 may transition to the first configuration. For example, proximal movement of member 50 may cause member 50 to partially unwind due to, for example, engagement of distal end portion 52 with one or more surfaces of lumen 20 and/or opening 22. Hub 60 may be omitted, and another actuation mechanism may be used to transition member 50 from the first configuration to the second configuration and from the second configuration to the first configuration.

Figure 3:
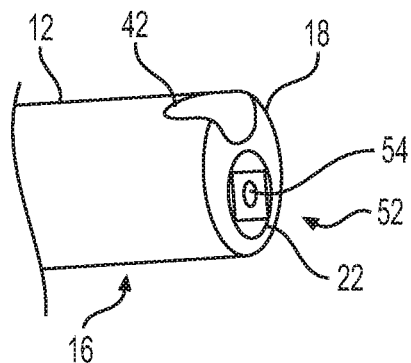
FIG. 3 shows a schematic view of a distal portion of an exemplary device in a first configuration.

FIG. 3 shows a close-up of distal end portion 16 with member 50 in the first configuration. Distal end portion 52 of member 50 may be oriented so that camera portion 54 faces distally out of opening 22. Distal end portion 52 may lie in a plane that is transverse to the longitudinal axis of insertion portion 12 and to the longitudinal axis of a proximal portion of member 50. Distal end portion 52 may lie in a plane that is parallel or substantially parallel to a plane of opening 22. As shown in FIG. 3, opening 42 of lumen 40 may be transverse to distal end face 18. For example, opening 42 may be an elongate opening which is disposed both on a side surface of insertion portion 12 and on a distal end face 18. For example, opening 42 may open to the side and distally.

Figure 4:
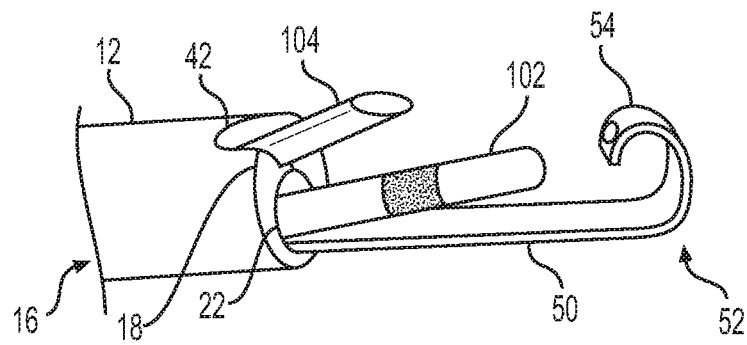
FIG. 4 shows a schematic view of a distal portion of an exemplary device in a second configuration.

FIG. 4 shows a close-up of distal end portion 16 in the second configuration. Distal end portion 52 of member 50 may be oriented so that camera portion 54 faces proximally and is extended distally of opening 22. Proximally-facing camera portion 54 may also face to the side, in this case upwardly. As shown in FIGS. 2 and 4, when member 50 is in the second configuration, member 50 may occupy only a small portion of lumen 20 and opening 22 so that a tool 102 may be inserted in lumen 20 along with member 50. For example, member 50 may lie along one side of lumen 20 such as a bottom side of lumen 20. Tool 102 may be any of a variety of tools for use in a body lumen of a patient. For example, tool 102 may be a probe such as an ultrasound probe, radio frequency probe, and/or cryogenic probe. Tool 102 may also be a forceps, a snare, a basket, a tome, a suction device, or any other type of diagnostic or therapeutic tool. The examples above are not exclusive; any type of tool or accessory may be used. The fact that tool 102 may be inserted into lumen 20 along with member 50 may mean that a diameter of insertion portion 12 may be smaller than conventional scopes because one lumen can be used for both a member 50 including camera portion 54 and a tool 102. A smaller diameter of insertion portion 12 may allow use of insertion portion 12 in narrower body lumens. For example, insertion portion 12 may be inserted into a subject's lungs, whereas other types of medical devices may be limited as to how far they can extend into a body lumen such as bronchial passages. In addition, because tool 102 and member 50 are narrower than insertion portion 12, they may reach further into body passages than insertion portion 12 may reach.

As also shown in FIG. 4, another tool 104 may be inserted into lumen 40 and may extend out of opening 44. Tool 104 may include any of the tools described in connection with tool 102. Tool 104 may exit opening 40 at an angle transverse to a longitudinal axis of insertion portion 12. Alternatively, tool 104 may exit opening 40 parallel to a longitudinal axis of insertion portion 12.

Figure 5:
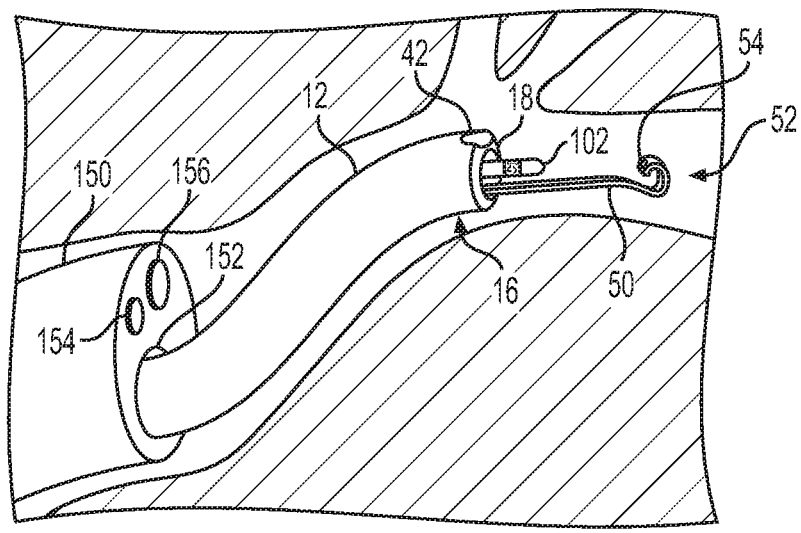
FIG. 5 shows a schematic view of a distal portion of an exemplary device in a body lumen.

FIG. 5 depicts medical device 10 in a body lumen. The body lumen shown in FIG. 5 is a bronchial lumen; however, device 10 may be used in any body lumen. Device 10 may optionally be used in conjunction with an introduction device 150. Introduction device 150 may be a scope, such as an endoscope, ureteroscope, bronchoscope, duodenoscope, or any other type of scope, catheter, or sheath. Introduction device 150 may have a larger diameter than device 10. Introduction device 150 may include a lumen 152. Lumen 152 may be sized so as to allow passage of medical device 10 through lumen 152. Introduction device 150 may also include other lumens 154, 156 through which other devices may be passed. Introduction device 150 may be advanced to a certain portion of a body lumen. Introduction device 150 may reach a point in a body lumen where device 150 is too large in diameter to pass further into the body lumen. Insertion portion 12 may be further advanced into the lumen. The small diameter of insertion portion 12 may facilitate advancing insertion portion 12 into a further and/or narrower portion of a body lumen than other scopes could reach. For example, as described above with regard to FIG. 4, because tool 102 and member 50 may occupy the same lumen 20, an outer diameter of insertion portion 12 may be smaller than if two separate lumens were required for tool 102 and member 50.

When a distal end portion 16 of device 10 is proximal of an area of interest, member 50 may be advanced into the second configuration, as shown in FIG. 5. In the second configuration, camera portion 54 may be directed toward an area of interest in a body lumen. For example, as shown in FIG. 5, an area of interest may be located between a distal face 18 of insertion portion 12 and distal portion 52 of member 50. Camera portion 54 may, for example, capture images of a side surface of a body lumen and/or of a central portion of a body lumen, proximal to a location of camera portion 54. Tool 102 may be deployed toward the area of interest. Tool 104 (FIG. 4) may also be deployed toward the area of interest. Tools 102 and/or 104 may be used to perform therapeutic and/or diagnostic procedures on an area of interest in a body lumen.

Figure 6:
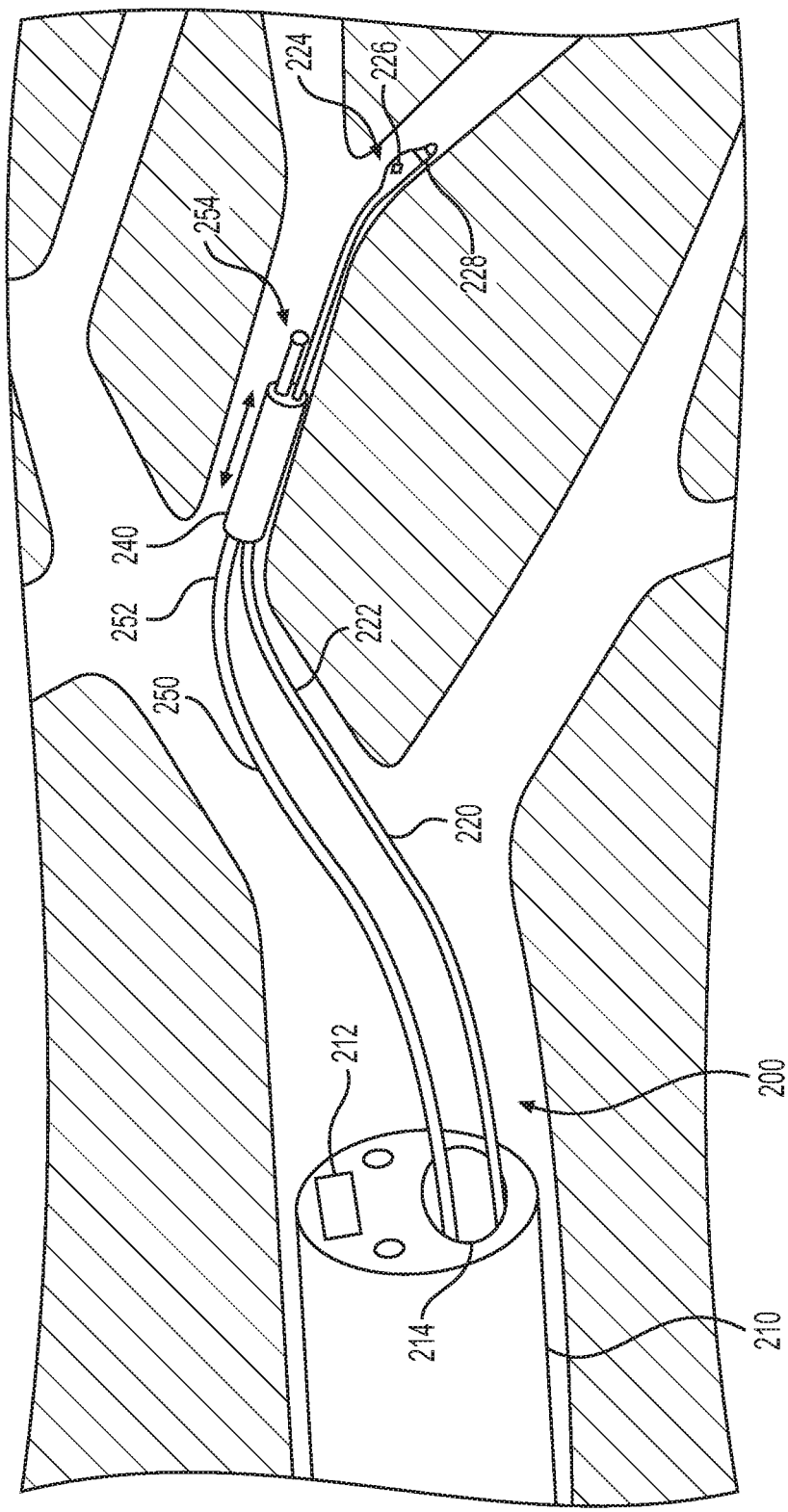
FIG. 6 shows a schematic view of a further exemplary device in a body lumen.

FIG. 6 shows another embodiment according to the present disclosure, which may be used in conjunction with or in an alternative to the aspects described above with regard to FIGS. 1-5. As shown in FIG. 6, a distal portion of a medical device 200 may include an insertion portion 210. Insertion portion 210 may have any of the qualities of insertion portion 12 or introduction device 150, described above. Insertion portion 210 may include a camera 212 to provide imaging of a body lumen of a subject. Insertion portion 210 may also include other features, such as illumination features (not shown). Insertion portion 212 may include a lumen 214. Lumen 214 may have any of the qualities of, for example, lumen 152.

A member 220 may be inserted through lumen 214 and may extend out of an opening at a distal end of lumen 214 and on a distal face of insertion portion 212. Member 220 may have any of the qualities of member 50, described above. In an alternative, member 220 may have differing qualities from member 50. For example, member 220 may have a round cross-section. Member 220 may include a shaft 222, which may extend from a proximal end (not shown) of insertion portion 210, through insertion portion 210, and out an end of insertion portion 210. Member 220 may be steerable (see, e.g., FIGS. 11A-11C, discussed in further detail below). For example, one or more steering mechanisms may be disposed within an inside lumen of member 220 or on an external surface of member 220. Member 220 may have a distal portion 224. Distal portion 224 may include an atraumatic tip. For example, an atraumatic tip may be formed from a soft durometer material, such as silicone, polyurethane, soft durometer pebax, or any other suitable material.

Distal portion 224 may include a camera portion 226 and/or an illumination portion. Camera portion 226 may be disposed in a lumen of distal portion 224 or on an exterior surface of distal portion 224. Distal portion 224 may be formed at least partially of transparent material. Camera portion 226 may incorporate an illumination mechanism. Camera portion 226 may include components such as lenses and imagers. Camera portion 226 may be mounted at an angle between 0 degrees and 70 degrees relative to a longitudinal axis of member 220. If camera portion 226 is mounted at an angle of 0 degrees, an end face of camera portion 226 (which, in one example, may include a planar surface of a cover, lens, or the like) may lie flat against the longitudinal axis of member 220, or may lie parallel to the longitudinal axis of member 220, such that the end face may face a sideways direction. The end face may, for example, face a direction perpendicular to the longitudinal axis of member 220. If camera portion 226 is angled with respect to the longitudinal axis of member 220, its end face may face either proximally (see, e.g., FIGS. 8A and 8B) or distally (see, e.g., FIGS. 9A, 10A, and 10B). The end face may, for example, face a direction transverse to, but not perpendicular to, the longitudinal axis of member 220. An angle of tilt may be measured between the end face of camera portion 226 and the longitudinal axis of member 220. Camera portion 226 may be at least partially proximally facing so that camera portion 226 may view an area proximal of camera portion 226. Camera portion 226 may also face in a lateral, or side, direction relative to member 220. In an alternative, camera portion 226 may face distally so that camera portion 226 may view an area distal to camera portion 226. Distal portion 224 may also include an anchor member 228. Anchor member 228 may be used to secure distal portion 224 in a body lumen of a subject at a location of interest. While anchor member 228 is shown being located distally of camera portion 226 in FIG. 6, other configurations are also available. For example, camera portion 226 may be located distally of anchor member 228.

A tether 240 may engage with shaft 222 of member 220. FIGS. 7A-7C, discussed in further detail below, show potential configurations of tether 240. Tether 240 may be slidable or otherwise longitudinally movable with respect to member 220. For example, tether 240 may slide along shaft 222 of member 220. Tether 240 may have a smaller cross-section than a cross-section of lumen 214, so that tether 240 can fit within lumen 214. Tether 240 may be capable of sliding proximally to a proximal portion of insertion member 210 and distally out of an opening of lumen 214. Tether 240 may be prevented from sliding distally past distal portion 224 of member 220. For example, distal portion 224 may be wide enough that tether 240 may not move past distal portion 224.

A tool 250 may also be inserted through lumen 214 and may extend out of an opening on a distal face of insertion portion 212. Tool 250 may include a shaft 252. Tether 240 may also engage with shaft 252 of tool 250. One or more surfaces of tether 240 may have an interference fit with one or more surfaces of tool 250. Movement of tether 240 longitudinally with respect to member 220 therefore may result in longitudinal movement of tool 250 with respect to member 220. Tool 250 may also have an atraumatic tip at a distal portion 254. An atraumatic tip of tool 250 may have any of the qualities of an atraumatic tip of member 210, discussed above. An atraumatic tip or other feature of tool 250 may prevent tether 240 from moving off of a distal end of tool 250, so that tool 250 may be stationary relative to tether 240.

FIGS. 7A-7C depict different exemplary cross-sectional configurations of tethers. As shown in FIG. 7A, an exterior surface 260 of tether 240 may have a circular cross-section. Such a circular cross-section is merely exemplary. Tether 240 may have any suitable cross-sectional shape. Tether 240 may have a lumen 262 formed therein. A shaft 222 of member 220 may be slidably disposed within lumen 262. Lumen 262 and shaft 222 may be sized and shaped so as to allow for translational sliding of tether 240 along shaft 222 of member 220 while tether 240 is coupled to shaft 252 of tool 250. For example, lumen 262 and shaft 222 may be sized and shaped so that there is a clearance fit between lumen 262 and shaft 222. While lumen 262 and shaft 222 are shown in FIG. 7A as having circular cross-sections, lumen 262 and shaft 222 may have any suitable shape and size. For example, shaft 222 may be keyed to lumen 262. Shaft 222 and/or lumen 262 may have an ovular, polygonal, or other shape. For example, shaft 222 and/or lumen 262 may have a hexagonal or star shape. Alternatively, member 220 may have any of the properties of member 50, described with regard to FIGS. 1-5 above, and tether 240 may be configured to work in conjunction with such a member. For example, shaft 222 may have a substantially flat shape (width substantially greater than thickness), and lumen 262 may have a corresponding substantially flat rectangular shape.

Tether 240 may also have another lumen 264 formed therein. Shaft 252 of tool 250 may be disposed within lumen 264. Shaft 252 and lumen 264 may be sized and shaped so as to have an interference fit or a slight interference fit with one another. The interference fit or slight interference fit may serve as a locking and/or mating mechanism between shaft 262 and lumen 264, securing the two together during translational movement relative to shaft 222. While lumen 264 and shaft 252 are shown in FIG. 7A as having a circular cross-section, lumen 264 and shaft 252 may have any suitable shape and size. For example, shaft 252 may be keyed to lumen 264. Shaft 252 and/or lumen 264 may have an ovular, polygonal, or other shape. One or both of shaft 252 and/or lumen 264 may additionally or alternatively have anchoring mechanisms which may prevent or limit translational movement between shaft 252 and lumen 264. When tether 240 moves longitudinally with respect to member 220, tool 250 may also move longitudinally with respect to member 220. While lumen 262 is shown as having a smaller cross-sectional diameter than lumen 264, lumen 262 may be larger than lumen 264, or lumens 262 and 264 may be the same size. While FIGS. 7A-7C depict shaft 222 as having a smaller diameter than shaft 252, shaft 222 may be the same size as shaft 252 or may be larger than shaft 222.

FIG. 7B depicts an alternative exemplary configuration of a tether denoted 240'. As shown in FIG. 7B, tether 240' may have an outer surface 270 and lumens 272, 274. Surface 270 may include side openings 276, 278 in communication with lumens 272, 274. Openings 276, 278 may extend from a proximal portion of tether 240' to a distal portion of tether 240'. Openings 276, 278 may be parallel to a longitudinal axis of tether 240'. Openings 276, 278 may be disposed approximately 180 degrees apart from one another. Alternatively, openings 276, 278 may be disposed at a smaller angle from one another. Opening 276 may have a width which is smaller than a diameter of shaft 222 of member 220. Opening 278 may have a width that is smaller than a diameter of shaft 252 of tool 250.

Shaft 222 of member 220 may be slidably disposed in lumen 272. Lumen 272 may have any of the properties of lumen 252, described above with regard to FIG. 7A. Tether 240 may have lip portions 280 at either side of opening 276. Lip portions 280 may be deformable so that shaft 222 may be pressed and/or snapped into lumen 272 via opening 276. Shaft 252 of tool 250 may be disposed within lumen 274. Lumen 274 may have any of the properties of lumen 264, described above with regard to FIG. 7A. Tether 240 may have lip portions 282 at either side of opening 278. Lip portions 282 may be deformable so that shaft 252 may be pressed and/or snapped into lumen 274 via opening 278. As described with regard to FIG. 7A, when tether 240 moves longitudinally with respect to member 220, tool 250 may also move longitudinally with respect to member 220. In an alternative, a tether may contain one lumen with an opening (for example, such as lumens 272 and 274) and one lumen without an opening (for example, such as lumens 262 and 264).

FIG. 7C depicts a further exemplary configuration of a tether 240". As shown in FIG. 7C, tether 240" may have a protruding surface 280 that is configured to engage with a broken lumen surface 282 of shaft 252 of tool 250. Shaft surface 282 and tether surface 280 may be sized and shaped so as to have an interference fit with one another so as to lock and/or mate to one another, securing the two together as tether 240" translates relative to member 220. Tether surface 280 may be pressed and/or snapped into a lumen defined by shaft surface 282. Shaft 252 may include surface 282 at only a distal portion 254 of tool 250, or shaft 252 may include surface 282 along a greater portion of a length of shaft 252, such as an entirety or a majority of shaft 252. While shaft surface 282 and tether surface 280 are shown in FIG. 7C as being rounded, shaft surface 282 and tether surface 280 may have any suitable shape and size. For example, shaft surface 282 may be keyed tether surface 280. Shaft surface 282 and/or tether surface 280 may have an ovular, polygonal, teardrop, or other shape. For example, shaft surface 282 and/or tether surface 280 may have a hexagonal, a triangular, or a star shape. One or both of shaft surface 282 and/or tether surface 280 may additionally or alternatively have anchoring mechanisms which may prevent or limit translational movement between shaft surface 282 and tether surface 280.

Tether 240" may also have a lumen 284. Lumen 284 may have any of the properties of lumens 262 and/or 272, described above with regard to FIGS. 7A-7B. A surface of tether 240" may include an opening 286 that is in communication with lumen 284. In an alternative, tether 240" may lack such opening 286 and lumen 284 may be similar to lumen 262, described above. Tether 240 may have lip portions 288 at either side of opening 286. Lip portions 288 may be deformable so that shaft 222 may be pressed and/or snapped into lumen 284 via opening 286. As described with regard to FIGS. 7A-7B, when tether 240" moves longitudinally with respect to member 220, tool 250 may also move longitudinally with respect to member 220.

Figure 8A:
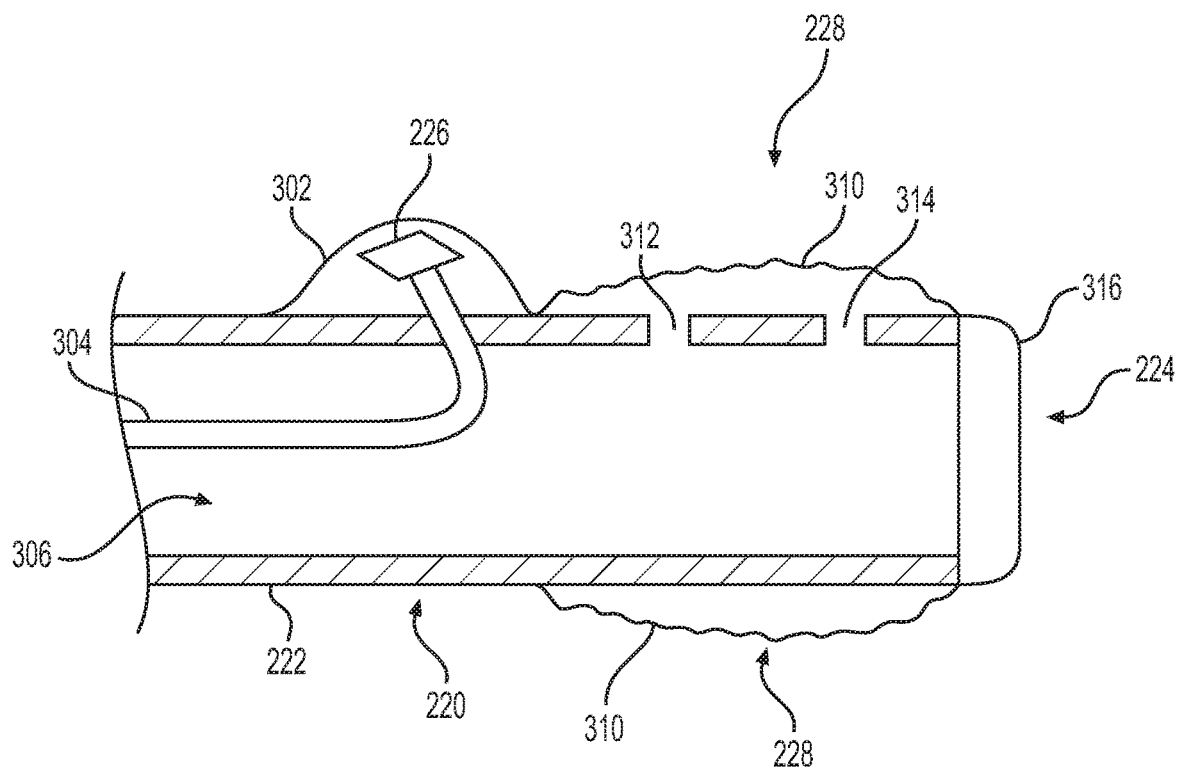
FIGS. 8A-8B show cross-sectional schematic views of a first exemplary anchoring mechanism.
Figure 8B:
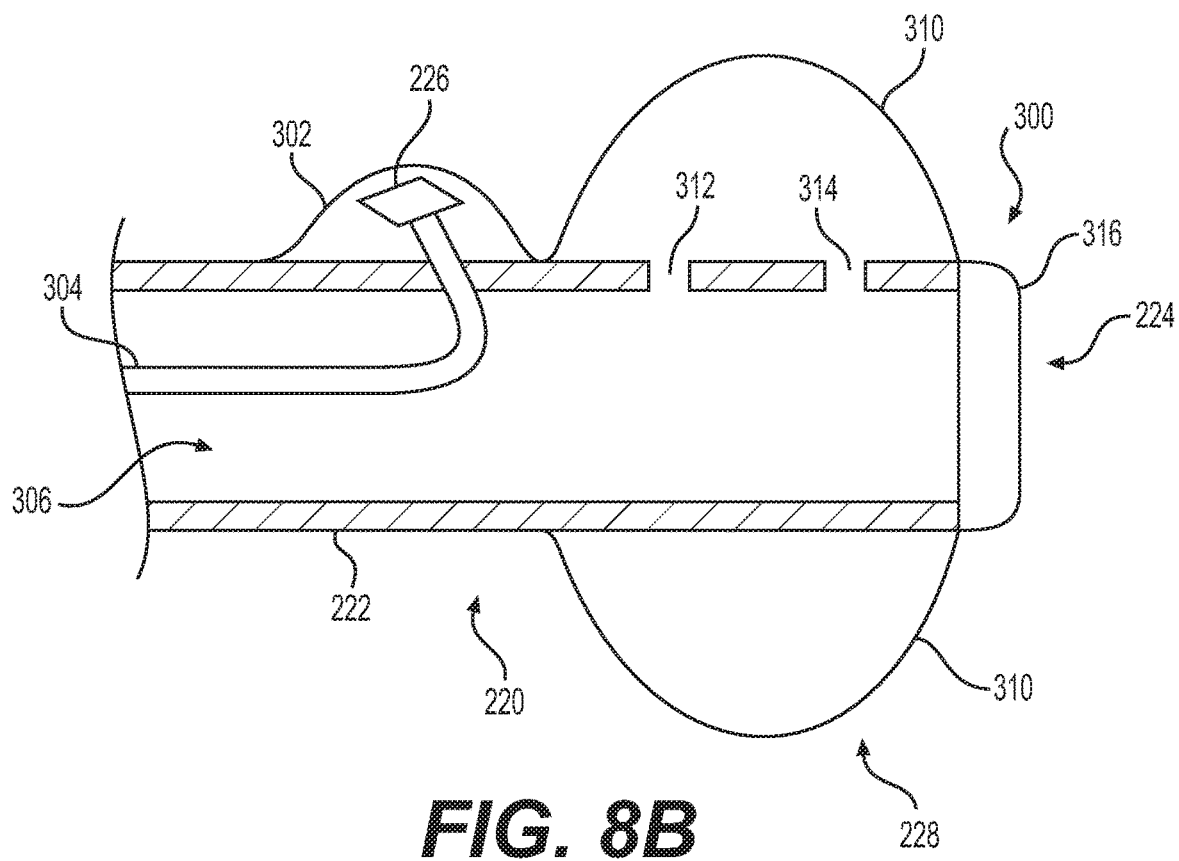

FIGS. 8A and 8B show exemplary distal portion 224 of member 220. Distal portion 224 may include a surface 302 defining a space that may contain camera portion 226. Surface 302 may be transparent. In an alternative, camera portion 226 may be disposed on any outer surface of shaft 222. Camera portion 226 may be connected to a cable 304 which may provide power and/or control signals to camera portion 226 and/or transmit images obtained by camera portion 226. Cable 304 may be disposed in a lumen 306 of member 220.

Anchor 228 may include an expandable member 310. FIG. 8A shows expandable member 310 in a collapsed configuration, and FIG. 8B shows expandable member 310 in an expanded configuration. Expandable member 310 may be an inflatable member such as a balloon. The wall of shaft 222 of member 220 may include openings 312, 314 therethrough. Openings 312 and 314 may be in communication with an interior of expandable member 310 and with lumen 306. Air, fluid, or another medium may be passed through lumen 306 and through openings 312 and 314 in order to expand expandable member 310. When expandable member 310 is in an expanded configuration (FIG. 8B), expandable member 310 may engage with walls of a body lumen, such as the body lumen shown in FIG. 6. Engagement of expandable member 310 with walls of a body lumen may serve to anchor member 220 in place so that member 220 may not be longitudinally movable when expandable member 310 is in an expanded configuration.

Expandable member 310 may have a variety of shapes and sizes. A longitudinal length of expandable member (along a longitudinal axis of member 220) as well as a radial width of expandable member (extending orthogonally from member 220) may be any suitable amount. For example, expandable member 310 may have a circular cross section having a diameter of approximately 4-5 mm. In an alternative, expandable member 310 may have a hexagonal cross section having a greatest width dimension of approximately 10 mm. Alternatively, expandable member 310 may have any other cross-sectional geometry and any diameter or cross-sectional size that is effective in anchoring member 220 to a body lumen in an expanded configuration. For example, a diameter or cross-sectional size of expandable member 310 may be approximately 2 mm-5 mm or 2 mm-6 mm. Expandable member 310 may be a non-compliant balloon formed of a semi-rigid material such as PEBAX, PET, or any other suitable material. Alternatively, expandable member 310 may be a compliant balloon formed of a soft durometer material such as silicone, polyurethane, or any other suitable material.

Figure 9A:
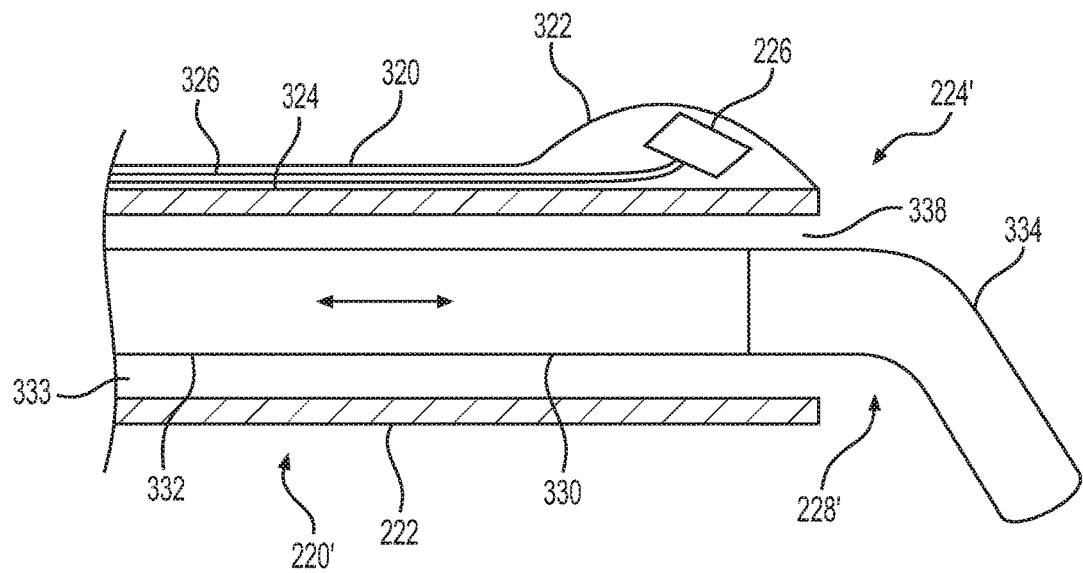
FIGS. 9A-9B show cross-sectional schematic views of a second exemplary anchoring mechanism.
Figure 9B:
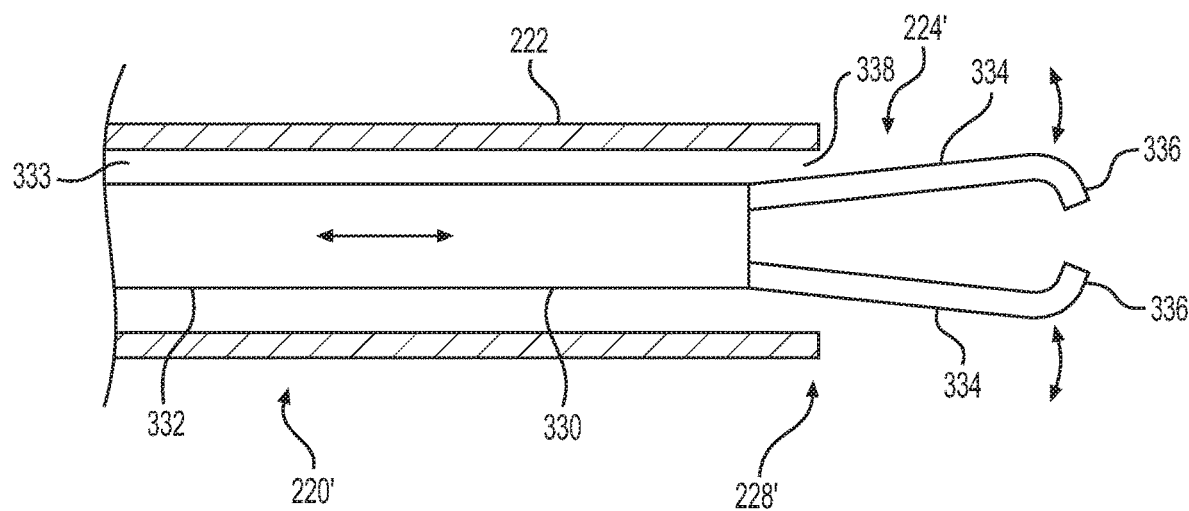

FIGS. 9A-9B show another exemplary distal portion 224' of member 220'. FIG. 9A shows a side view of distal portion 224', and FIG. 9B shows a top view of distal portion 224' rotated 90 degrees relative to FIG. 9A. Distal portion 224' may include a surface 320, which along with surface 324 of member 220', defines a lumen that may contain camera portion 226 and a cable 326. Surface 320 may project radially outward to form a surface 322 near camera portion 226. Surfaces 320 and/or 322 may be transparent. In addition or in an alternative, camera portion 226 may be disposed on a surface of shaft 222 (such as surface 324). Camera portion 226 may be connected to cable 326, which may provide power and/or control signals to camera portion 226 and/or transmit images from camera portion 226. Surface 320 may extend proximally from distal portion 224' so that cable 326 passes through a lumen defined by surface 320 instead of a central lumen (such as lumen 333) of member 220'. In an alternative, cable 326 may pass through lumen 333.

Anchor 228' may include a clipping mechanism 330. Clipping mechanism 330 may include a control member 332. Control member 332 may be slidably disposed in a lumen 333 of shaft 222 so that control member 332 and other portions of clipping mechanism 330 may move longitudinally relative to shaft 222. A distal portion of control member 332 may be fixed to a proximal portion of a pair of jaws 334. Jaws 334 may include curved end portions 336. End portions 336 may curve toward one another. Jaws 334 may be moved laterally relative to one another so that they may be opened and closed. Jaws 334 may be biased toward an open configuration. For example, a shape of jaws 334 may be such that jaws 334 are biased in an open configuration and/or jaws 334 may be made of material having shape memory. In a first configuration, control member 332 and jaws 334 may be disposed within a lumen of shaft 222. In the first configuration, jaws 334 may be in a closed position resulting from pressure exerted by walls of lumen 333 on jaws 334. In a closed position, tips 336 of jaws 334 may contact one another, may be near to one another, or may overlap one another. Control member 332 may be slid longitudinally relative to shaft 222 so that jaws 334 extend completely through a distal opening 338 of lumen 333 in a second configuration. After clipping mechanism 330 is moved into the second configuration, jaws 334 may be in an open position due to the bias of jaws 334 and the absence of pressure from the walls of lumen 333. In an open configuration, there may be a gap (or a relatively larger gap) between tips 336.

In order to achieve an anchoring function such as via clamping jaws 334, control member 332 may be retracted into a third configuration so that a proximal end of jaws 334 is within lumen 333. The pressure of the walls of lumen 333 and/or opening 338 on the proximal ends of jaws 334 may cause tips 336 of jaws 334 to move toward one another. Body tissue that is between tips 336 of jaws 334 when the clipping mechanism 330 is transitioned to the third configuration may be pinched by tips 336 and/or other portions of jaws 334 in the third configuration. Closing jaws 334 around tissue may result in anchoring of clipping mechanism 330 and member 220 to the tissue. Jaws 334 may angle away from a longitudinal axis of lumen 333 so that tips 336 extend past an exterior surface of shaft 220, toward a side surface of a body lumen, as shown in FIG. 9A. Jaws 334 may each diverge from the longitudinal axis of lumen 333 so that jaws 334 are substantially parallel to one another. Angling of jaws 334 away from the longitudinal axis of lumen 333 may facilitate engagement of jaws 334 with tissue on a size surface of the body lumen.

Figure 10A:
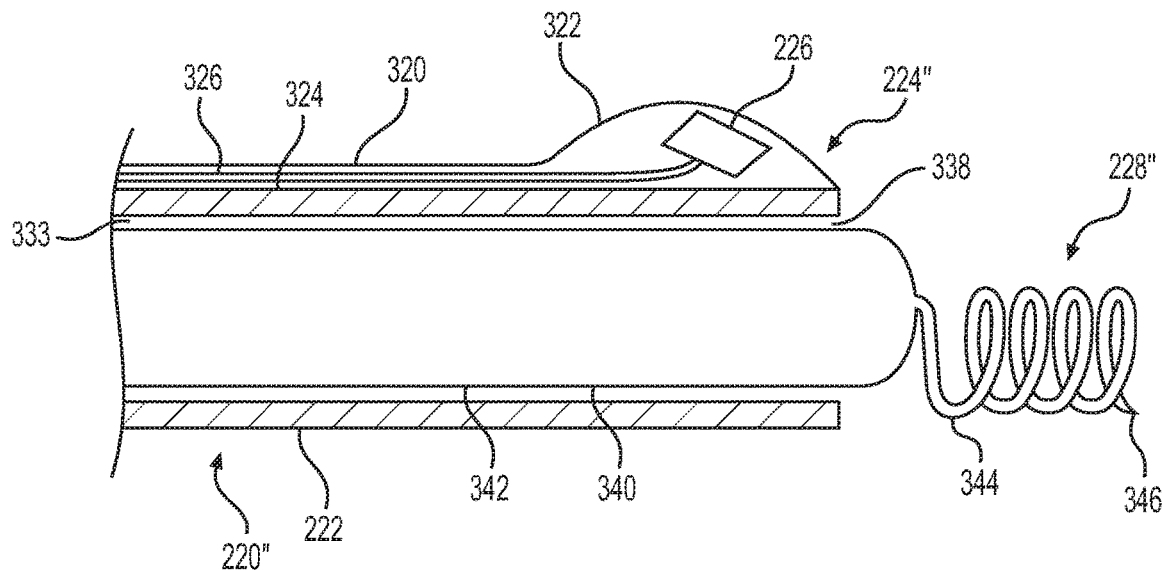
FIGS. 10A-10B show cross-sectional schematic views of a third exemplary anchoring mechanism.
Figure 10B:
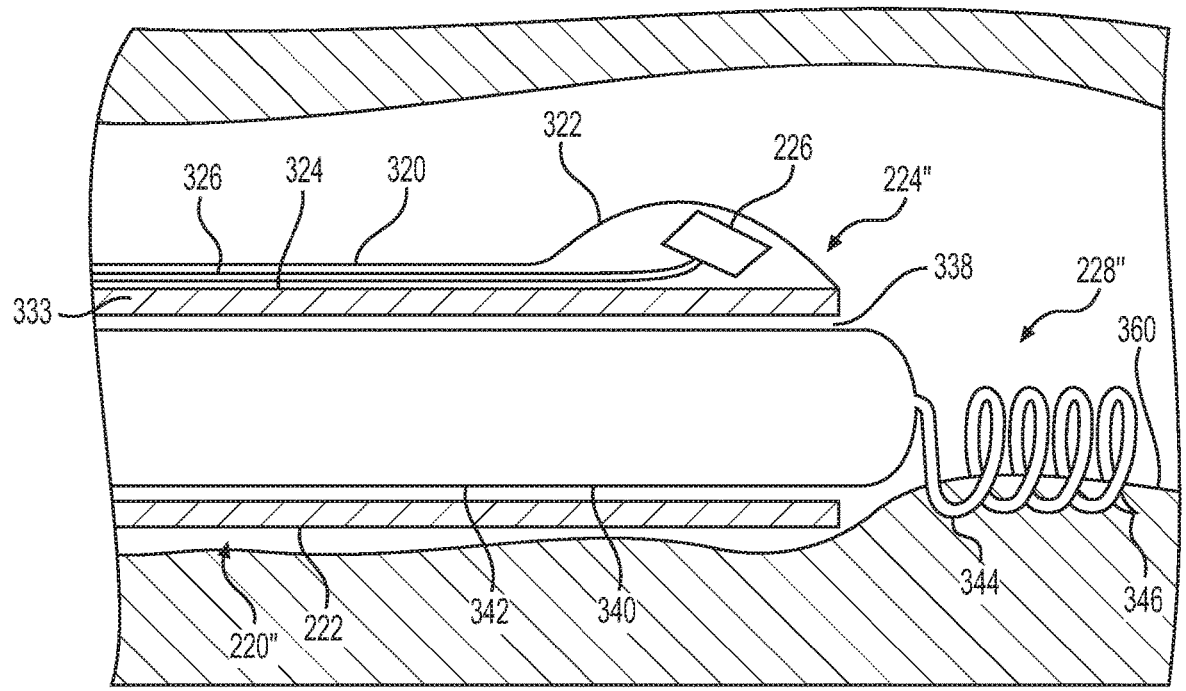

FIGS. 10A-10B depict another exemplary distal portion 224" of member 220". The example of FIGS. 10A and 10B may be similar to the example of FIGS. 9A and 9B, except with respect to the features described below. Anchor 228" may include an auger member 340. Auger member 340 may have an elongated control member 342 disposed within lumen 333 of shaft 222. Control member 342 may be rotatable relative to shaft 222. A distal portion of control member 342 may be attached to a coil 344. Coil 344 may be a corkscrew-type coil that may have one, two, four, or any other suitable number of coils. A distal end of coil 344 may include a pointed tip 346 that may be sharp. Control member 342 may be longitudinally movable relative in lumen 333 relative to shaft 222 so that coil 344 may be retracted into lumen 333 and extended out of opening 338 in lumen 333. Coil 344 may be made of a wire and may be made from, for example, stainless steel, elgiloy and other cobalt-containing alloys, nitinol, titanium, platinum or any other suitable material that may be formed into a coil shape and may have requisite stiffness to maintain the shape and to move through a tissue of a subject.

Auger member 340 may be transitioned from a first configuration to a second configuration. In a first configuration (FIG. 10A), coil 344 may be navigated to a target site within a lumen of a subject. Coil 344 then may rest against a wall 360 of a body lumen without engaging the tissue of the wall 360. Auger 340 may be transitioned to a second configuration (FIG. 10B) by rotating control member 342 about its own axis. Rotation of control member 342 may cause rotation of coil 344. Pointed tip 346 of coil 344 may pierce a tissue surface of a wall 360 of the body lumen. Continued rotation of control member 342 may cause pointed tip 346 to pass through tissue before exiting into the body lumen again. Coil 344 may continue to pierce and/or pass through the tissue with continued rotation of control member 342. Engagement of coil 344 with the tissue may cause member 220" to be fixed in a desired location in the body lumen.

Figure 11A:
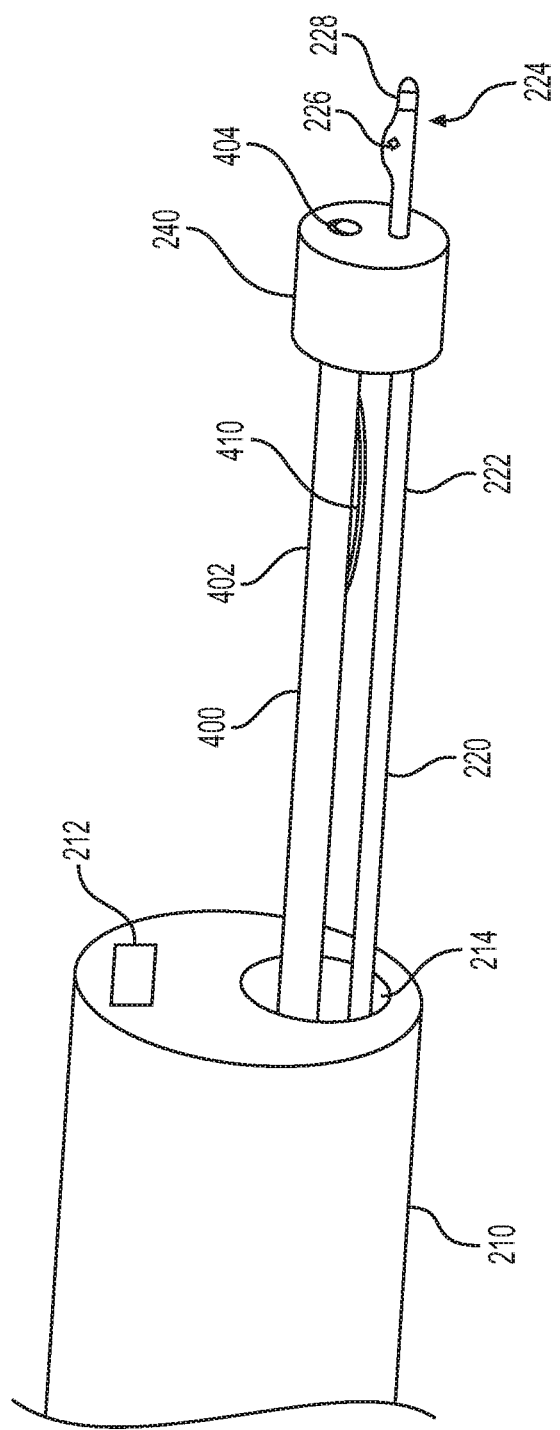
FIGS. 11A-11C show exemplary steering mechanisms.
Figure 11B:
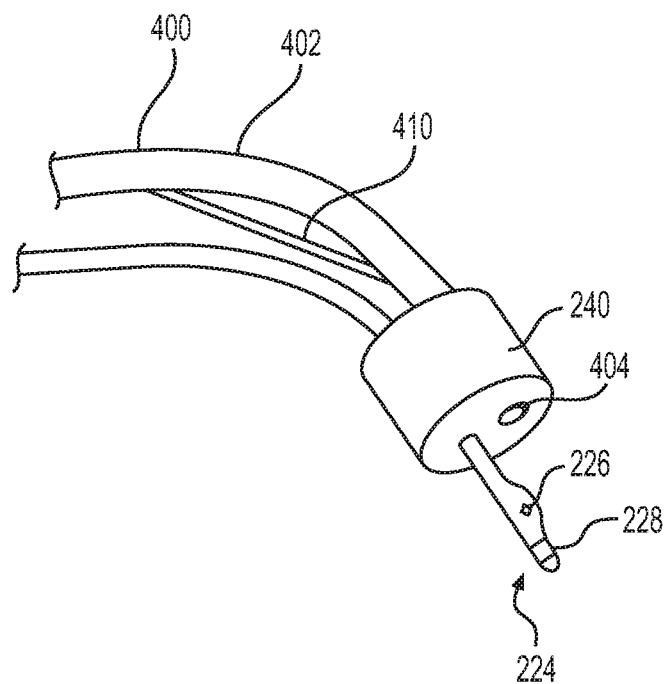
Figure 11C:
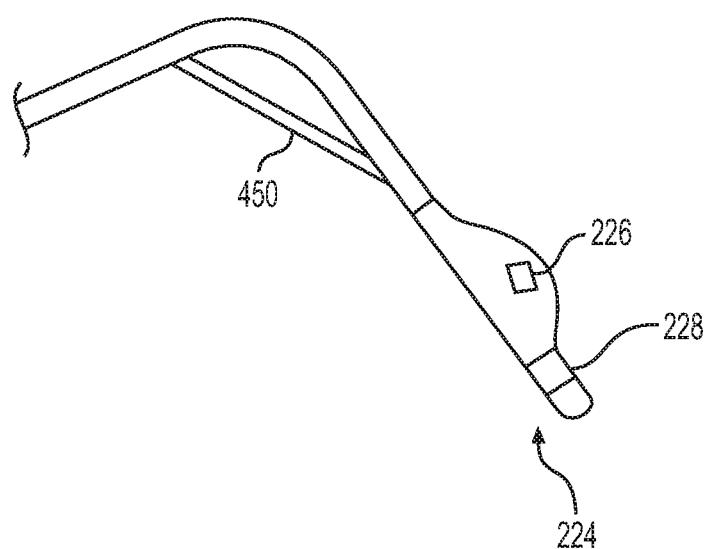

FIGS. 11A-11C depict exemplary steering mechanisms. As shown in FIG. 11A, member 220 (like member 220 in FIG. 6) may be navigated to a desired location by a steering member 400. Steering member 400 may be coupled to tether 240 (like tether 240 in FIG. 6). For example, shaft 402 of steering member 400 may be inserted into a lumen of tether 240. An end cap portion 404 of steering member 400 may restrain steering member 400 so that it remains coupled with tether 240. Steering member 400 may have an interference fit with a lumen of tether 240. Steering member 400 may have any of the properties of tool 252, described above, including those described with regard to FIGS. 7A-7C. Tether 240 may also have any of the properties described above, including those described with regard to FIGS. 7A-7C. Steering member 400 may also have a steering mechanism 410 that may be disposed inside of steering member 400 (e.g., in a lumen of shaft 402) or outside of shaft 402. FIG. 11A depicts an exemplary embodiment wherein steering mechanism 410 is disposed within a lumen of shaft 402 for a portion of a length of shaft 402 and is disposed outside of shaft 402 at another portion of a length of shaft 402. Steering mechanism 410 may exit shaft 402 via a hole near the distal end of shaft 402. Steering mechanism 410 may be, for example, a wire or a cable or any other suitable mechanism. Member 220 may also be slidably secured to tether 240, using any of the methods or mechanisms described above.

After steering member 400 and member 220 are coupled to tether 240, steering member 400, member 220, and tether 240 may be advanced through a lumen 214 of an insertion portion 210. Interaction between tether 240 and distal portion 224 of member 220 (e.g., the distal end of tether 240 abutting the proximal end of an enlarged portion of distal portion 224) may cause member 220 to be advanced along with tether 240 and steering member 400. Steering member 400, member 220, and tether 240 may extend out of a distal opening of lumen 214 and advanced distally of insertion portion 210. A relatively smaller size of tether 240, steering member 400, and member 220 may allow those components to reach narrower body lumens, such as bronchial lumens, than could be reached by insertion portion 210.

Steering mechanism 410 may extend proximally through a lumen 214 of insertion portion 210 to a control device. Actuation of steering mechanism 410 may cause bending of a distal portion of steering member 400, as shown in FIG. 11B. For example, actuation of steering mechanism 410 may cause a shortening of steering mechanism 410. After steering member 400 is used to position member 220 in a desired location of a subject's body lumen, member 220 may be anchored using anchor member 228. Steering member 400 and tether 240 may then be retracted through lumen 214 so that an operator may detach steering member 400 from tether 240. A tool 250 may then be secured to tether 240 and advanced through lumen 214 of insertion portion 210. Member 220 may act as a guidewire for tether 240 and tool 250. Tether 240 may ride along shaft 222 of member 220 so that tool 250 can be transported to a location of interest, proximate to distal portion 224 of member 220. Tool 250 may then be used to conduct a variety of diagnostic or treatment procedures on a subject. Tool 250 may eventually be retracted through lumen 214 and replaced by another tool 250, using the method described above. The above process may be repeated any number of times. At the end of a procedure, anchor portion 228 may be disengaged so that member 220 is no longer secured to a body lumen of a subject. Member 220 may then be retracted through lumen 214.

FIG. 11C shows an exemplary alternative configuration wherein member 220 includes a steering mechanism 450 such as a steering wire or cable or any other suitable mechanism. Steering mechanism 450 may have any of the properties of steering mechanism 410, described above. Steering mechanism 450 may be disposed inside of member 220 (e.g., in a lumen of shaft 222) or outside of shaft 222. FIG. 11C depicts an exemplary embodiment wherein steering mechanism 450 is disposed within a lumen of shaft 222 for a portion of a length of shaft 222 and is disposed outside of shaft 222 at another portion of a length of shaft 402. Actuation of steering mechanism 450 may cause bending of a distal portion of member 220, as shown in FIG. 11C. For example, actuation of steering mechanism 450 cause a shortening of steering mechanism 450.

In use, member 220 may be advanced toward a desired location of a subject's body lumen. Steering mechanism 450 may aid in such positioning. Member 220 may then be anchored using anchor member 228. A tool 250 may then be secured to tether 240. Tether 240 may be secured to member 220 if it is not already secured to member 220. Tool 250 and tether 240 may then be advanced through lumen 214 of insertion portion 210. Member 220 may act as a guidewire for tether 240 and tool 250. Tether 240 may ride along shaft 222 of member 220 so that tool 250 can be transported to a location of interest, proximate to distal portion 224 of member 220. Tool 250 may then be used to conduct a variety of diagnostic or treatment procedures on a subject. Tool 250 may eventually be retracted through lumen 214 and replaced by another tool 250, using the method described above. The above process may be repeated any number of times. At the end of a procedure, anchor portion 228 may be disengaged so that member 220 is no longer secured to a body lumen of a subject. Member 220 may then be retracted through lumen 214.

While principles of the present disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A medical device comprising:
   a handle portion;
   an insertion portion having a proximal end portion at the handle portion, wherein the insertion portion includes a lumen therein and a distal end having a distal opening in communication with the lumen; and
   a member disposed within the lumen, the member having a distal end portion with an imaging device;

wherein the member is configured to transition between a first configuration and a second configuration, wherein, in the first configuration, the distal end portion of the member is angled to form an L-shape relative to a more proximal portion of the member adjacent to and proximal of the distal end portion, such that the imaging device faces distally, and, in the second configuration, the imaging device faces proximally, and wherein extending the distal end portion of the member distally past the distal opening causes the member to transition from the first configuration to the second configuration.

2. The medical device of claim 1, wherein the member includes a flat shaft having a cross sectional width greater than a thickness and having at least one substantially planar outer surface.

3. The medical device of claim 2, wherein the shaft and a distal end of the shaft is ribbon shaped.

4. The medical device of claim 2, wherein the imaging device is disposed on a side surface proximal to a distal end of the member.

5. The medical device of claim 1, wherein, in the second configuration, the distal end portion of the member forms a curl shape.

6. The medical device of claim 1, wherein the member is configured to transition between the first configuration and the second configuration by moving the member longitudinally relative to the lumen.

7. The medical device of claim 6, wherein a proximal portion of the member is coupled to a hub, and wherein the hub is configured to effect longitudinal movement of the member relative to the lumen as the hub translates relative to the handle portion.

8. The medical device of claim 1, wherein the member includes a shaft and a second lumen extending from a proximal end of the shaft to a distal end of the shaft, wherein the second lumen terminates in a second distal opening at the distal end of the shaft.

9. The medical device of claim 8, wherein the second distal opening terminates at an angle transverse to a longitudinal axis of the shaft.

10. The medical device of claim 1, wherein a cross-section of the member is circular.

11. The medical device of claim 1, wherein the member is comprised of a shape memory material.

12. The medical device of claim 1, further comprising a tool disposed within the lumen.

13. A medical device comprising:
a shaft having a lumen extending from a proximal end of the shaft to a distal end of the shaft, wherein the lumen terminates in a distal opening at the distal end of the shaft; and
a member disposed within the lumen, the member having a ribbon shape with a terminal end and an imaging device spaced from the terminal end, wherein the member is configured to transition between a first configuration and a second configuration, wherein, in the first configuration, a distal end portion of the member is proximal to the distal opening of the shaft and the distal end portion of the member forms an L-shape relative to a more proximal portion of the member adjacent to and proximal of the distal end portion, such that the imaging device faces distally, and, in the second configuration, the imaging device faces proximally, and wherein extending the distal end portion of the member distally past the distal opening causes the member to transition from the first configuration to the second configuration.

14. The medical device of claim 13, wherein the member comprises a second lumen extending from the proximal end to the distal end, wherein the second lumen terminates in a second distal opening at the distal end of the shaft.

15. The medical device of claim 14, wherein the second distal opening terminates at an angle transverse to a longitudinal axis of the shaft.

16. The medical device of claim 13, wherein the ribbon shape has a cross sectional width greater than a thickness and at least one substantially planar outer surface.

17. The medical device of claim 13, further comprising a tool disposed within the lumen.

18. The medical device of claim 13, wherein, in the second configuration, the distal end portion of the member forms a curl shape.

19. The medical device of claim 13, further comprising a handle portion coupled to a proximal portion of the shaft, wherein a proximal portion of the member is coupled to a hub, and wherein the hub is configured to effect longitudinal movement of the member relative to the lumen as the hub translates relative to a handle portion.

20. The medical device of claim 13, wherein the member is comprised of a shape memory material.

* * * * *